United States Patent [19]

Leveson et al.

[11] 4,413,185
[45] Nov. 1, 1983

[54] SELECTIVE PHOTOIONIZATION GAS CHROMATOGRAPH DETECTOR

[75] Inventors: Richard C. Leveson, Willowdale; Nicholas J. Barker, Don Mills, both of Canada

[73] Assignee: Her Majesty the Queen in right of Canada, as represented by the Minister of National Defence, Ottawa, Canada

[21] Appl. No.: 258,575

[22] Filed: Apr. 29, 1981

[51] Int. Cl.³ .............................................. H01J 37/00
[52] U.S. Cl. ................................................ 250/423 P
[58] Field of Search .......................... 250/288, 423 P; 73/23.1

[56] References Cited

U.S. PATENT DOCUMENTS 2,950,387  8/1960  Brubaker .................... 250/423 P
2,959,677  11/1960 Robinson et al. ............ 250/423 P
4,239,967  12/1980 Carr et al. ................... 250/288

Primary Examiner—Bruce C. Anderson
Attorney, Agent, or Firm—Cushman, Darby & Cushman

[57] ABSTRACT

The invention disclosed is a detection system for the detection of gaseous or vaporous ionizable chemical species entrained in air as a carrier gas. The system includes a gas chromatograph column for separating the chemical species to be detected and a photoionization detector designed for use with air as the carrier gas.

13 Claims, 5 Drawing Figures

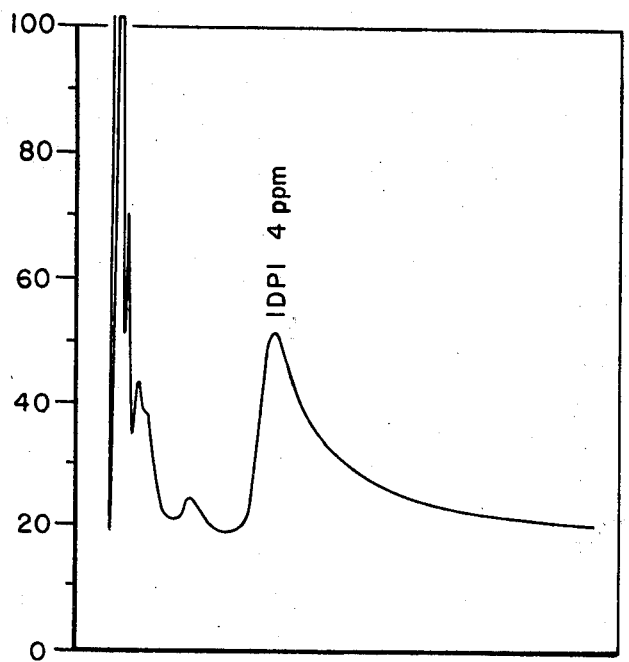
FIG. 3 ISOPHORONE-Di-ISOCYANATE (IDPI) 4 ppm SAMPLE IN .25 ml AIR
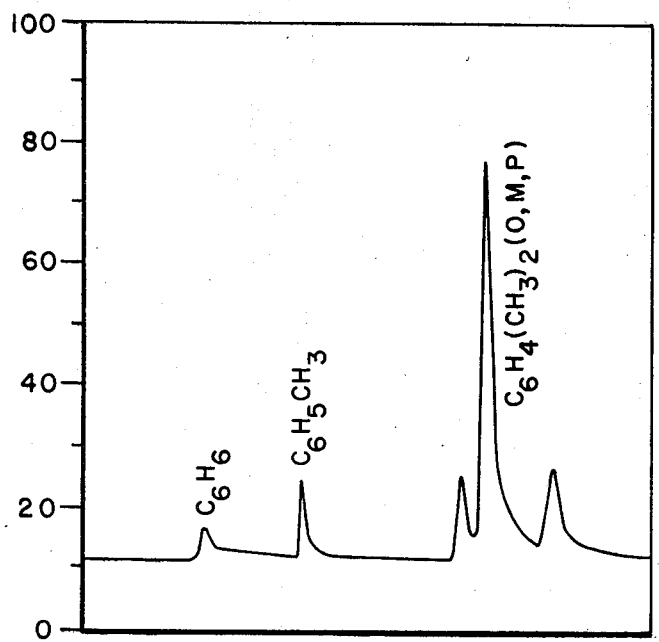
FIG. 5 XYLENES WITH BENZENE AND TOLUENE CONTAMINATION. CHART SPEED: 2cm/min. 2.5 μl INJECTION

SELECTIVE PHOTOIONIZATION GAS CHROMATOGRAPH DETECTOR

BACKGROUND OF THE INVENTION

1. Field of the Invention

This invention relates to the detection of gaseous or vaporous ionizable chemical species in a photoionization detector, and in particular to a detection system in which the chemical species are detected using air as a carrier gas.

2. Description of the Prior Art

Photoionization detectors are often designed for use at the end of a gas chromatograph column and use radiation in the vacuum ultraviolet region of the spectrum to ionize chemical species borne into an ionization chamber from the column in a carrier gas. The photon energy of the radiation is at a level designed to ionize only the chemical species to be detected and not the carrier gas. Ionization is detected by electrodes in the ionization chamber electrically connected to an electrometer.

In gas chromatography, a carrier gas, which in the prior art for use in ionization detectors is generally an inert gas, flows continuously through a chromatograph column. A gaseous or liquid diluent, containing the ionizable chemical species under study, is introduced into the end of the chromatograph column remote from the detector. Component species elute through the column at different rates and are thus separated before reaching the detector. Such chemical species enter the ionization chamber of a photoionization detector in the carrier gas, become ionized, and give rise to a response from the electrometer. When displayed on a chart recorder each response appears as a peak whose arrival time depends upon the time taken for that particular contaminant to elute through the column before being ionized. By comparison with known standards the species can be identified and their quantity measured by determining the area under the peak displayed on the chart recorder.

The radiation used in a photoionization detector should be of high enough energy to ionize the chemical species to be detected, but not so high as to discernably ionize the carrier gas or any other species present which it is not desired to detect. Generally speaking the radiation used is ultraviolet radiation between 1000 A° to 2000 A°. Such radiation is of a low enough photon energy that it will not ionize any of the permanent air gases, such as oxygen, nitrogen, carbon dioxide, the inert gases or water vapour.

Such radiation is quickly absorbed in air and it will penetrate more than a few millimeters only in a vacuum or an atmosphere of inert gas. Thus it is commonly referred to as vacuum ultraviolet radiation.

The radiation source which is commonly used in photoionization detectors is a gas discharge tube made of glass and metal and filled with a suitable gas at low pressure. A crystal window composed of an appropriate transmissive material provides an exit for the vacuum ultraviolet radiation. In prior art, photoionization detectors have employed a discharge tube in which the discharge or excitation produced is by maintaining a high potential direct current across two metal electrodes located within the tube and in contact with the gas.

In a discharge tube of the above type, complicated tube designs have to be used in order to prevent electrode metal from being removed by ion impact in the process known as "sputtering". Such electrode metal is deposited upon the inner surface of the crystal window, thereby drastically reducing the transmission through said window and hence the operating life of the tube.

For example in Driscoll U.S. Pat. No. 3,933,432 issued Jan. 20, 1976, the high intensity portion of the gas discharge has been confined to a central capillary within the discharge tube by constraining the flow of ions as they move from one electrode to another. In this way, high ion current densities result in the central capillary but only very low ion current densities are established at the electrode surfaces. Where the effects of sputtering are controlled in this way, intensity and distribution of radiant flux must necessarily be heavily compromised, with resultant deterioration of the sensitivity of the detector.

The abovementioned design results in what is effectively a "point source" of vacuum UV radiation, originating from the small cross section of the capillary. As a result of this configuration, the distribution of radiative flux across the diameter of the ion chamber in any plane perpendicular to the direction of travel of the radiation entering the chamber is highly non-uniform, being high in the centre and low at the periphery. Apart from the reduced ionization due to limited total flux, such a design will exhibit strong "quenching" effects whenever a trace of oxygen is present in the chamber. Quenching occurs when an electron, generated as a result of photoionization, becomes attached to an oxygen atom, due to the high electron affinity of oxygen. The resulting negative ion has a mobility far lower than the original electron, and a far greater likelihood than an electron that it will recombine with a positively charged ion before it can be detected. Where a point source light is used a larger percentage of the oxygen ions migrate out of the field of ionizing radiation and recombine before they can be detected. Thus quenching will be a severe problem if a device utilizing such a source should be required to operate using air as carrier gas.

Discharge tubes have been built, for other applications, in which the metal electrodes are mounted external to an all-glass tube (fitted with an appropriate crystal window) and are connected to a supply of radio-frequency power. The radio frequency radiation is coupled capacitively into the gas and excites a discharge therein without the aforementioned sputtering effect. In prior art, such as Young U.S. Pat. No. 3,996,272, such tubes have been designed with one electrode being inserted into a hollow re-entrant capillary tunning up the axis of the cylindrical discharge cavity. The second electrode is formed from a metal cylinder, wrapped around the outside of the tube. The resulting coaxial electrode configuration functions as a capacitor. Tubes of this type are relatively difficult and expensive to make and, due to obstruction by the re-entrant capillary, do not have a radially uniform output intensity.

SUMMARY OF THE INVENTION

According to the invention, a detector system is contemplated for the detection of gaseous or vaporous ionizeable chemical species entrained in air as a carrier gas, said system comprising a source of high purity air as a carrier gas; a gas chromatograph column for separating the chemical species to be detected; conduit means for connecting said source of high purity air to one end of said chromatograph column; valve means associated with said conduit means for controlling the flow of air to said column; injection port means in said conduit between said valve means and said one end of the chromatograph column for injecting a sample containing said chemical species into said carrier gas; and a photoionization detector.

The photoionization detector includes a gas discharge tube and a cylindrical ionization chamber including electrodes for detecting the ionization of the chemical species, wherein the carrier gas containing the chemical species to be detected is flowed through said ionization chamber and is ionized by UV radiation from said discharge tube, said UV radiation being axially directed from said discharge tube into said ionization chamber such that the radiation intensity is substantially uniform in any plane of the ionization chamber perpendicular to the direction of radiation into the chamber.

BRIEF DESCRIPTION OF THE DRAWINGS

In the drawings:

FIGS. 3-5 are graphs illustrating the sensitivity of the detector system according to the invention.

DETAILED DESCRIPTION OF THE INVENTION

Figure 1:
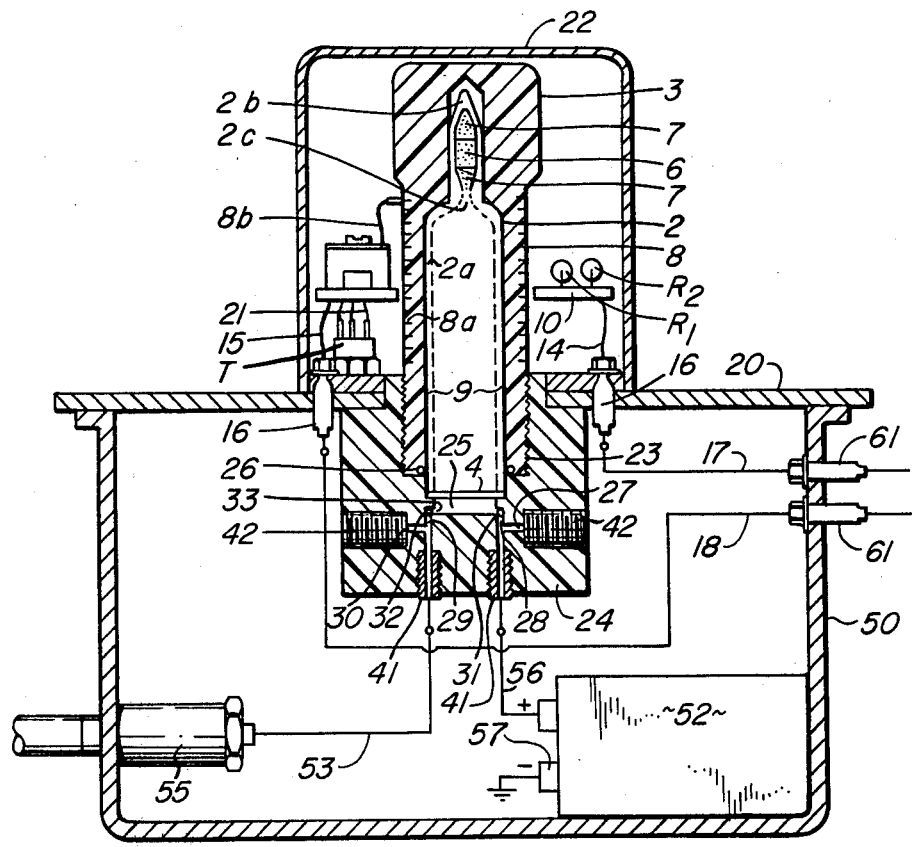
FIG. 1 is a longitudinal sectional view of a preferred photoionization detector, for use in a detector system according to the invention.

In FIG. 1, a gas discharge tube is illustrated. Specifically, a glass gas discharge tube 2 is held in a cylindrical holder 3 of an electrically insulating material, with low dielectric loss, such as polytetrafluoroethylene (sold under the trade-mark Teflon). The discharge tube 2 has a main cylindrical portion 2a measuring ½ inch in its outside diameter and ⅜ inch in its inside diameter and approximately 1¾ inches in length. At one end, the cylindrical portion is bonded to a ½ inch diameter by 1 millimeter thick crystal window 4, made from magnesium fluoride, lithium fluoride, barium fluoride, strontium fluoride, calcium fluoride or sapphire. The window is bonded to the tube either by the use of silver chloride, applied at high temperature to platinized surfaces on the glass and crystal or by the use of a suitable silicone or epoxy adhesive. The other end of the cylindrical portion of the discharge tube tapers to a terminal portion 2b having an outside diameter of ¼ inch and a length of approximately ⅜ inch and ending in a sealed point. A constriction 2c is formed between the main and terminal portions of the tube in order to retain, within the terminal portion, a getter compound 6 composed of finely divided barium metal. The barium is secured in place by two plugs of glass wool 7. The tube is filled with an inert gas e.g. krypton, xenon or argon gas at a pressure of from 0.1 to 5 Torr. Preferably, the gas is krypton at a pressure of about 3 to 3.5 Torr.

The tube 2 does not contain internal electrodes. Rather, a coupling inductor 8 is wound around a spiral groove in the outside of the holder 3. One end 8a of the inductor penetrates the holder and makes contact with a metal foil strip 9 coaxially wrapped around the inner wall of the holder 3. The width of the strip is between ½ and 1 inch and its purpose is to shape the electromagnetic field and aid in the firing of the discharge tube. The foil strip should be positioned at the crystal end of the tube and should not be so wide as to substantially block radio frequency radiation, emerging from the inductor 8, from coupling into the discharge. The other end of inductor 8b runs to an annular printed circuit board 10 which encircles the holder 3 and carries some parts of the oscillator circuit which includes a radio frequency transistor T, a tuning capacitor C, resistors R1 and R2, and other components not shown in FIG. 1.

Both power supply leads 14 and 15 pass to the annular circuit board 10 through two radio frequency interference filters 16 (sold under the trade mark Filtercon by Erie Co.) 28 Volt DC power is supplied to the circuit via leads 17 and 18. The filters 16 are mounted on a metal bulkhead 20 which supports the photoionization detector.

The transistor T is screwed into the metal bulkhead 20 for heat sinking purposes. Flying leads 21 connect T to the circuit board 10. As shown in FIG. 1, a deep metal cup 22 is positioned over the gas discharge tube assembly and, together with the metal bulkhead 20, shields the system from both leakage outwards of radio frequency radiation and from leakage inwards of stray electromagnetic radiation. The holder 3 is provided with a screw thread 23 at its lower end and this portion of the holder penetrates the metal bulkhead 20 and screws into an electrically insulating body 24, made from, for example polytetrafluoroethylene (Teflon trade mark). The body 24 forms a cylindrical ionization chamber 25 which is closed at one end by the window 4 of the discharge tube 2. The surfaces of the chamber 25 are thus of an electrically insulating, chemically inert material.

In order to prevent leakage between the chamber 25 and the discharge tube 2, a silicone-rubber O-ring is provided as a seal 26. This is held in compression by screwing the holder 3 firmly in place.

Access to the chamber 25 is provided through gas inlet channels 27 and 28. The gas is exhausted through outlet channels 29 and 30. Both the inlet and outlet channels 27 and 30 terminate in conventional threaded fittings 42. The inlet 28 and outlet 29 are disposed such that the gas flow therebetween is substantially perpendicular to the longitudinal axis of the chamber 25.

Detector electrodes 31 and 32 are disposed in chamber 25.

Electrode 31 is preferably the anode and is positioned in the ionization chamber at the inner end of the gas entrance channel 28. Electrode 32 is preferably the cathode and is positioned in the ionization chamber 25 opposite the cathode at the inner end of gas exit channel 29. It is preferable to have the cathode in very close proximity to the ionizing region in order to enhance ion collection efficiency; simultaneously the cathode should be screened from direct impingement of ultraviolet radiation, otherwise an undesirable photoelectron current will be generated.

The electrodes 31 and 32 are made of platinum wire and in the electrode configuration shown are located inside a recess 33 machined around the cylindrical wall of the ionization chamber 25 in such a manner that ultraviolet radiation from the discharge tube 2 does not impinge directly upon them.

The electrodes are preferably in the form of two symmetrically opposed semi-circular wires placed circumferentially in the ionization chamber recess 33. At points within the body 24 away from the immediate vicinity of the detection chamber, the electrode leads are routed through channels 40 separated from the carrier gas passages 27, 28, 29 and 30 and exit from the body via two gas-tight threaded plugs 41. The gas entrance and exit channels 27 and 30 terminate at two gas-fittings (not shown) which screw into receptacle openings 42. Other alternative arrangements of the electrodes are possible.

The ionization chamber 25 is in the form of a cylinder 2 mm long (measured axially) with a diameter approximately equal to the internal diameter of the tube 2.

A metal casing or cover 50 is positioned around the body 24 and secured with screws to the metal bulkhead 20 in such a manner as to complete the screening of the photoionization detector from external stray fields. Apart from enclosing the body 24, cover 50 is made sufficiently large to enclose an ambient temperature gas chromatograph column, a chromatographic injection port or sample-loop system, and a high voltage power supply or dry batteries 52 at approximately 200 volts DC. The cathode electrode lead 53 passes through the housing 50 using a special low leakage radio frequency interference filter 55 and hence passes to an electrometer (not shown).

The carrier gas inlet and outlet and outlet connection (not shown) penetrate the cover 50 through standard metal bulkhead gas fittings. The access port for the injection port (not shown) or the sample-loop system (not shown) also penetrate the metal bulkhead 20 and the cover 50. The positive terminal of the power supply or batteries 52 is connected to the anode electrode lead 56 while the negative terminal 57 is connected to ground.

Leads 17 and 18 from the circuit board 10 penetrate the cover 50 via radio frequency interference filters 61 to supply power to the oscillator circuit (not shown).

Figure 2:
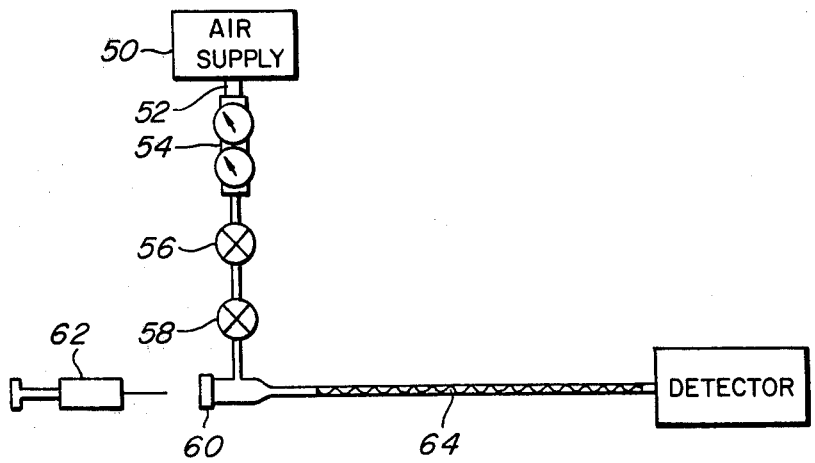
FIG. 2 is a schematic diagram of the detector system according to the invention.

As best seen in FIG. 2, a source of high purity air, preferably extra dry grade e.g. Linde Air Ultra Zero having less than 0.1 ppm total organic contamination, is stored in a lecture bottle 50. If available, any suitable external air supply may be employed. The lecture bottle is connected by conventional fittings to a gas conduit 52. Gas pressure through the conduit is controlled by a two-stage (dual guage) pressure regulator 54. Downstream of regulator 54 is a valve means, preferably two metering needle valves, a first 56 for coarse adjustment and a second 58 for fine adjustment. Downstream of the valve means is an injection port in the form of a septum 60 through which a gaseous sample, ranging in size of from about 1 milliliter to 1 microliter in volume, containing the chemical species to be detected is introduced into the stream of air (carrier gas) flowing through conduit 52, typically by means of a hypodermic syringe 62. The interchangeable septum employed is a Teflon ® faced, silicon rubber material of 0.25″ diameter a Hamilton Micro Sep ®F-138, available in Canada from Chromatographic Specialties, has been found suitable.

A sample loop (not shown) which provides for continuous injection of contaminant chemical species may also be provided.

Downstream of the septum 60, conduit 52 is connected to one end of a conventional gas chromatograph column 64. The other end of the chromatograph column includes a fitting for connection to input channel 27 of detector via fitting 42. Column lengths of from 15 m (6″) to 6 m (20′) of 3.2 mm (⅛″) diameter, operating at ambient temperature are typically employed. A four foot SE-30 5% on 60–80 mesh chromosorb ®G column has been found suitable.

A continuous stream of air is passed through the column at a flow rate of 10±1 ml/minute wherein the chemical species are separated.

The said species are ionized in the ionization chamber 25 by UV radiation from the discharge tube 2 and accelerated by an electric field between the detector electrodes 31 and 32 and the positively ionized species are collected by one of the electrodes wired as a cathode. The collected ions produce a response on an electrometer (not shown). When displayed on a chart recorder (not shown), each response appears as a peak whose arrival time depends upon time taken for that particular species to elute through the column before being ionized.

The inner surfaces of the system, including injection port, chromatograph column, ionization chamber, including all conduits and fittings in contact with the air supply containing the chemical species to be detected are of a chemically inert material such as teflon ® to permit analysis of reactive compounds such as $H_2S$.

As mentioned above, the photoionization detector according to the invention will register any compound whose ionization potential is less than a certain specified threshold and this threshold is selected so that none of the natural air gases register because of their higher ionization potentials. In this manner, a vast number of organic (and some inorganic) gases and vapors may be detected. Certain halogenated organics having very high ionization potentials can be detected presumably because of the readiness with which they form negative ions.

There are no hard and fast criteria which can be applied to determine whether a given compound is suitable for detection. It may be stated that the majority of volatile organics are readily detectable as well as some inorganic gases.

Two criteria have been found to be of some value are as follows:
1. Is the ionization potential of the compound less than 10.6 eV i.e. the approximate photon energy of the VUV lamp emission?
2. Is the boiling point of the compound too high for its elution through an ambient temperature gas chromatograph column to be feasible?

Having stated the first criterion, this must immediately be qualified. While any compound whose ionization potential is less than 10.6 eV can be sensed by the detector, a great many compounds whose ionization potentials are greater than this can also be detected. These include a very large number of organic halides, including chloroform and the Freons ®, whose ionization potentials may exceed 12 eV. These compounds are sensed because of their electrophillic nature and are detected by a mechanism analogous to electron capture. Propane and butane, with respective ionization potentials of 11.1 eV and 10.63 eV are detectable with excellent sensitivity although the reason for this is still not fully understood.

The second criterion is more difficult to apply: some compounds with boiling points in excess of 200° C. are readily detectable. FIG. 3 shows the result of injecting a 4 ppm sample of isophorone-di-isocyanate into the instrument, set to attenuation factor 10. Despite the fact that this compound has a boiling point in excess of 200° C., it is potentially detectable to 10 ppb.

Figure 4:
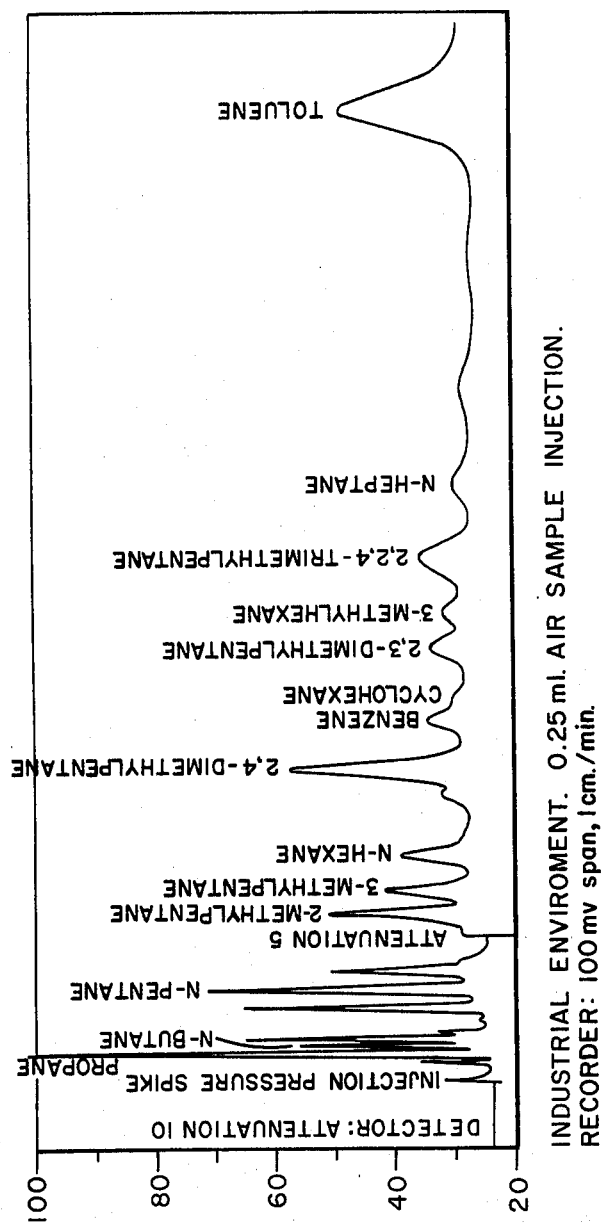

FIG. 4 shows a typical analysis of an occupational environment, a 0.25 ml sample of air from an industrial unit located next door to an automotive upholsterer exhibits a very wide variety of alkanes and aromatics mainly characteristic of gasoline and of the adhesives being employed. In order to appreciate the scale of the measurement it should be noted that the effective sensitivity is 25 times that of the calibration measurement (not shown). In the light of this, it is apparent that typical levels exhibited in FIG. 4 are in the range 5 to 100 ppb and no health standards are apparently being violated.

An analysis, such as that in FIG. 4 above, can be performed with the detector system in approximately 10-15 minutes and the full results are obtained on-the-spot, so that any follow-up can be made immediately.

Headspace samples may be taken from above contaminated water or other liquids, from biological or forensic samples. Chloroform and gasoline, for example, are easily detected in contaminated drinking water to levels which would normally require far more costly and time-consuming instrumental technique.

The detector is not restricted to organic gases and vapours; sulphur gases, such as hydrogen sulphide and carbon disulphide (and the mercaptans) can be detected with great sensitivity.

FIG. 5 shows an analysis of 5 ppm xylene (from a technical solvent grade) in which traces of benzene and toluene are clearly visible and the three isomers of xylene are completely resolved. This particular determination was carried out in a space of just $3\frac{1}{2}$ minutes, using one of the new technology fused-quartz capillary columns manufactured by Contrast this with the traditional method, which must be performed in the laboratory and which will often take a skilled person up to 1 hour to complete.

Breath analysis is a fascinating new field to which the detector system may be applied. Volatile drug metabolites (e.g. carbon di-sulphide from disulfuram) can be readily detected and elimination studies carried out on solvent levels present in the breath of exposed workers.

Although by no means exhaustive, the following detectable compounds are noteworthy: vinyl chloride, chloroform, alkanes e.g. propane and cyclohexane, alkenes e.g. ethylene and benzene, hydrogen sulphide, carbon disulphide, methylchloride, ethylene chlorides, halothane, xylenes, nitric oxide, ethylacrylate, mercaptans and freons ® a trademark for a series of halogenated hydrocarbons typically used in aerosol propellants.

In use, the krypton gas in the tube is excited across the entire cross-sectional area of said tube and the radiation intensity is substantially uniform in any plane of the chamber perpendicular to the direction of travel of radiation entering the chamber, said radiation including light-intensities of about $10^{15}$ photons per second at about 1236 A° and about $10^{14}$ photons per second at about 1165 A°. This is achieved by exciting the krypton gas inductively from outside the tube by the use of a coil connected to a radio frequency oscillating circuit. The inductance coil is provided around the outside of the tube and acts like an antenna in coupling electromagnetic radiation into the gas tube to excite the gas within by induction.

Inductive excitation by radio frequency oscillation eliminates the need for electrodes in the gas tube itself, and thus sputtering is not a problem.

Thus, inductive coupling excites the gas in the tube across the entire cross-sectional area of the tube and thus produces a high radiation level of uniform intensity across this area. This area and the transmissive area of the window, both approximate the cross-sectional area of the ionization chamber. The sensitivity of the detector is increased because there is no dead space in the ionization chamber. Where the carrier gas is air, a portion of this radiation will be absorbed as it enters the chamber. Nevertheless, while decreasing towards the rear of the chamber, the radiation intensity is substantially uniform in any plane of the chamber perpendicular to the direction of travel of radiation entering the chamber. This significantly reduces quenching, and thus air can be effectively used as a carrier gas. This is very desirable when the detector is to be used to detect trace chemical species in air. The carrier gas used in the chromatograph column is purified air, and the air sample containing the species to be detected can simply be passed through the chromatograph column and into the photoionization detector. Thus there is no disruptive effect from the air sample which introduces the species to be detected into the chromatograph column.

Thus with the krypton tube described herein, it is possible to deliver simultaneously light intensities of approximately $10^{15}$ photons per second at the 1236 A° wavelength and approximately $10^{14}$ photons per second at the 1165 A° wavelength although the mechanism is not entirely known. The result of this high intensity is that a larger percentage of the chemical species are ionized and remain ionized and are captured by the detector electrodes.

The detection electrodes in the ionization chamber are connected to a D.C. power source whereby a voltage potential is applied across the electrodes. The electrodes are preferably arranged in the ionization chamber such that the lines of force of the electrostatic field created between the two electrodes are in a plane substantially perpendicular to the line of travel of the light radiation entering the chamber from the radiation source. Variations from this arrangement will reduce the effectiveness of the device. An electrometer or the like is electrically connected to the detection electrodes.

Since inductively coupled radio frequency excitation is used, care must be taken to eliminate stray electromagnetic waves from interfering with the electrometer circuitry. Thus, a metal casing around the inductor and the detector is advisable as well as the appropriate use of radio frequency interference filters to prevent the release of radio frequency waves from the inductor, which waves might interfere with the operation of the electrometer.

In view of the preferred embodiments described above, it should be apparent to those skilled in the art that the present invention may be embodied in forms other than those specifically described herein without departing from the spirit or central characteristics of the invention. Thus, the specific embodiments described herein are to be considered as illustrative and by no means restrictive.

We claim:

1. A detector system, for use in the detection of gaseous or vaporous ionizeable chemical species entrained in air as a carrier gas, said system comprising:
   a source of high purity air as a carrier gas;
   a gas chromatograph column for separating the chemical species to be detected from a mixture of said carrier gas and an ambient air sample containing said chemical species;
   conduit means for connecting said source of high purity air to one end of said chromatograph column;
   valve means associated with said conduit means for controlling the flow of air to said column;

injection port means in said conduit between said valve means and said one end of the chromatograph column for injecting a sample containing said chemical species into said conduit in gaseous or vaporous form to provide said mixture and a photoionization detector, said detector including a cylindrical ionization chamber, said ionization chamber being closed at one end by a crystal window composed of a transmissive material and including electrodes for detecting the ionization of the chemical species and an external gas discharge tube disposed adjacent to and in alignment with said window, wherein the mixture is flowed through said ionization chamber to ionize the chemical species by continuous UV radiation from said discharge tube, said UV radiation being axially directed from said discharge tube into said ionization chamber through said window such that the radiation intensity is substantially uniform in any plane of the ionization chamber perpendicular to the direction of radiation into the chamber.

2. A detector system according to claim 1, wherein said electrodes are arranged such that the lines of force of an electrostatic field created between said electrodes is substantially perpendicular to the axial radiation.

3. A detector system according to claim 2, wherein the discharge tube is a krypton gas discharge tube, producing UV radiation of light-intensities of about $10^{15}$ photons per second at about 1236 A° and about $10^{14}$ photons per second at about 1165 A°.

4. A detector system according to claim 1 or 2, wherein the gas in said discharge tube is at a pressure of about 0.1 to 5 Torr.

5. A detector system according to claim 3, wherein the gas in said discharge tube is at a pressure of about 3.5 Torr.

6. A detector system according to claim 1, said valve means is adjusted to provide a continuous rate of flow of air of $10 \pm 1$ ml/min through the system.

7. A detector system according to claim 6, wherein gas inlet and outlet means are provided in said ionization chamber, being arranged such that the flow of gas therebetween is substantially perpendicular to the longitudinal axis of said ionization chamber.

8. A detector system according to claim 7, wherein all surfaces downstream of said injection port means in contact with the contaminated carrier gas are of a chemically inert material.

9. A detector system according to claim 8, wherein the chemically inert material is polytetrafluoroethylene.

10. A method for the detection of gaseous or vaporous ionizable chemical species entrained in air as carrier gas, said method comprising:

(a) providing a source of high purity air as carrier gas;

(b) connecting said source of high purity air to one end of a gas chromatograph column;

(c) connecting the other end of said gas chromatograph column to a photoionization detector, said detector comprising a cylindrical photoionization chamber, said ionization chamber being closed at one end by a crystal window composed of a transmissive material and including electrodes for detecting the ionization of ionizable chemical species, and an external gas discharge tube disposed adjacent to and in alignment with said window;

(d) continuously flowing said high purity air through said column and said detector to provide a carrier gas stream;

(e) injecting a gaseous or vaporous sample containing said chemical species into said gas stream upstream of said gas chromatograph column;

(f) ionizing said chemical species in said photoionization chamber by axially directing continuous UV radiation from said external gas discharge tube into said chamber through said window such that radiation intensity is substantially uniform in any plane of the chamber perpendicular to the direction of radiation into the chamber; and (g) detecting the ionization of said chemical species.

11. A method according to claim 10, wherein the rate of flow of air through said system is $10 \pm 1$ ml/minute.

12. A method according to claim 11, wherein the sample size is from 1 milliliter to 1 microliter.

13. A method according to claim 10, wherein the UV radiation is of light-intensities of about $10^{15}$ photons per second at about 1236 A° and about $10^{14}$ photons per second at about 1165 A°.

* * * * *